(12) United States Patent
Wandke et al.

(10) Patent No.: US 9,345,120 B2
(45) Date of Patent: May 17, 2016

(54) ELECTRODE ARRANGEMENT FOR A BARRIER PLASMA

(71) Applicant: CINOGY GmbH, Duderstradt (DE)

(72) Inventors: Dirk Wandke, Heilbad Heiligenstadt (DE); Mirko Hahnl, Berlingerode (DE); Matthias Kopp, Gieboldehausen (DE); Leonhard Trutwig, Duderstadt (DE); Karl-Otto Storck, Duderstadt (DE)

(73) Assignee: Cynogy GmbH, Duderstadt (DE)

( * ) Notice: Subject to any disclaimer, the term of this patent is extended or adjusted under 35 U.S.C. 154(b) by 0 days.

(21) Appl. No.: 14/419,671

(22) PCT Filed: Jul. 18, 2013

(86) PCT No.: PCT/DE2013/000392
§ 371 (c)(1),
(2) Date: Feb. 5, 2015

(87) PCT Pub. No.: WO2014/023276
PCT Pub. Date: Feb. 13, 2014

(65) Prior Publication Data
US 2015/0216026 A1  Jul. 30, 2015

(30) Foreign Application Priority Data
Aug. 7, 2012 (DE) .......................... 10 2012 015 482

(51) Int. Cl.
*A61M 37/00* (2006.01)
*H05H 1/24* (2006.01)
(Continued)

(52) U.S. Cl.
CPC .............. *H05H 1/2406* (2013.01); *A61B 18/14* (2013.01); *A61N 1/0408* (2013.01); *A61N 1/40* (2013.01); *A61B 2018/00083* (2013.01); *A61B 2018/00452* (2013.01); *A61B 2018/00583* (2013.01);
(Continued)

(58) Field of Classification Search
CPC .................... H05H 1/2406; H05H 2001/2418; H05H 2245/123; H05H 2277/10; A61N 1/0408; A61N 1/40; A61B 18/14; A61B 2018/00083; A61B 2018/1465; A61B 2018/00452; A61B 2018/00583; A61B 18/18; A61B 18/02; A61B 18/12
See application file for complete search history.

(56) References Cited

U.S. PATENT DOCUMENTS 6,413,255 B1  7/2002 Stern
7,141,049 B2 * 11/2006 Stern ...................... A61B 18/14
606/41

(Continued)

FOREIGN PATENT DOCUMENTS

DE  4240272    6/1994
DE  10127035 A1  2/2002
(Continued)

*Primary Examiner* — Donald Raleigh
(74) *Attorney, Agent, or Firm* — Whitham Curtis Christofferson & Cook, PC

(57) ABSTRACT

An electrode arrangement for forming a dielectrically impeded plasma between an active surface of a flexible, planar electrode that can be connected to a high voltage source has a planar, flexible dielectric that forms the active surface which is connected to the planar electrode to form an electrode element where the electrode is completely covered towards to surface to be treated. The electrode arrangement is adaptable to irregular surfaces using a contact with surface elasticity for pressing onto the rear face of the electrode element facing away from the surface such that the electrode element by local deformation is automatically adapted to the irregularities.

12 Claims, 1 Drawing Sheet

(51) Int. Cl.
  *A61B 18/14* (2006.01)
  *A61N 1/40* (2006.01)
  *A61N 1/04* (2006.01)
  *A61B 18/00* (2006.01)

(52) U.S. Cl.
  CPC . *A61B2018/1465* (2013.01); *H05H 2001/2418* (2013.01); *H05H 2245/123* (2013.01); *H05H 2277/10* (2013.01)

(56) References Cited

U.S. PATENT DOCUMENTS

2004/0251240 A1  12/2004  Simon et al.
2011/0130752 A1* 6/2011  Ollivier .............. A61B 18/1492
                                                        606/33
2011/0313417 A1  12/2011  De La Rama et al.
2012/0259270 A1* 10/2012  Wandke ............... A61N 1/0408
                                                        604/23

FOREIGN PATENT DOCUMENTS

| | | |
|---|---|---|
| DE | 19532105 | 11/2002 |
| DE | 102006011312 | 10/2007 |
| DE | 102009060627 | 6/2011 |
| DE | 202010004332 | 12/2011 |
| WO | WO 2006/116252 | 11/2006 |
| WO | WO 2011/076193 | 6/2011 |
| WO | WO 2012/065125 | 5/2012 |

* cited by examiner

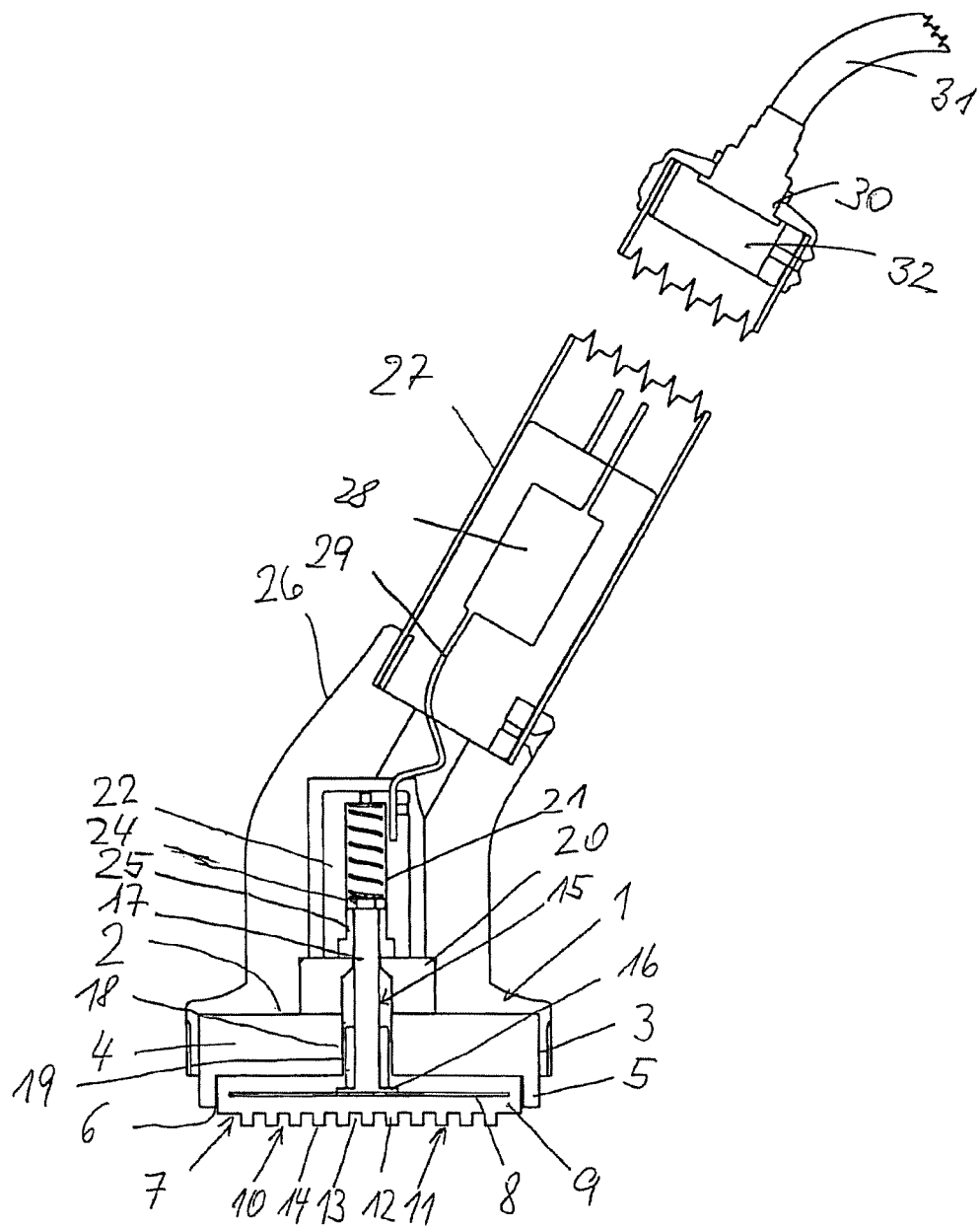

ELECTRODE ARRANGEMENT FOR A BARRIER PLASMA

FIELD OF THE INVENTION

The invention relates to an electrode arrangement for forming a dielectrical barrier plasma between an effective surface of the electrode arrangement and a surface which acts as a counterelectrode, having a flexible, flat electrode which can be connected to a high-voltage source, and having a flat, flexible dielectric which forms the effective surface and is connected to the flat electrode to form an electrode element and completely covers the electrode with respect to the surface which is to be treated.

BACKGROUND

It is known that surfaces of workpieces, but also skin surfaces, can be advantageously treated in various respects by plasma discharges. Surfaces of workplaces can be activated for a subsequent surface treatment, for example coating, in order to allow the coating to adhere better. It is further possible to clean surfaces with plasma discharges, for example to remove layers of oil.

A dielectrical barrier plasma discharge further allows skin surfaces to be safely treated. As a result, wound areas can be allowed to heal more quickly, the skin surface can be activated for improved absorption of active skincare or healing substances etc., for example.

The problem of being able to carry out plasma treatment which is as uniform as possible arises with surfaces which have an irregular three-dimensional shape. DE 195 32 105 C2 makes provision for a negative to be formed with the dielectric from the surface of the workpiece, said dielectric therefore comprising a plastic which can be shaped, for example can be pressed or thermoformed. In this case, provision is further made for an intermediate layer to be used, so that the dielectric can be shaped immediately at the surface of the workpiece with the intermediate layer. The intermediate layer is then removed in order to ensure there is an intermediate space, in which the plasma can form, between the dielectric and the electrode. On its face which is averted from the surface which is to be treated, the dielectric is coated with a conductive material which forms the electrode and to which the required high-voltage can be supplied in the form of an alternating voltage.

An electrode arrangement of the kind cited in the introductory part is known from DE 10 2009 060 627 A1. In the case of this electrode arrangement, the dielectric is formed by a flexible flat material which, on its face which faces the surface which is to be treated, is provided with a structure in order to form air guidance regions when the dielectric rests on the surface which is to be treated. The flat electrode is of flexible design and is fastened to the dielectric such that a layer of the dielectric shields the electrode from the surface which is to be treated. In particular, the electrode can be completely surrounded by the material of the dielectric, wherein only a high-voltage connection is routed out of the dielectric. The known electrode arrangement is particularly suitable for treating the skin surface of a human or animal body for carrying out a therapeutic or, in particular, cosmetic treatment. Owing to the resulting improved absorption capacity of the skin for active cosmetic substances, cosmetic treatments, such as smoothing out wrinkles, reducing the size of the pores etc., are possible in an efficient manner. Furthermore, a bactericidal and fungicidal effect of the plasma treatment can also be utilized for treating healthy or wounded areas of skin.

The flexible design of the known electrode arrangement allows adjustment to the irregularly shaped surface. If elastic restoring forces are not excessively high in this case, the electrode arrangement maintains its deformation. However, the ability to adapt to small local irregularities of the surface is limited in this case.

SUMMARY

The present invention is based on the object of improving an electrode arrangement of the kind mentioned in the introductory part in respect of the ability to adapt to surfaces with an irregular shape.

In order to achieve this object, an electrode arrangement of the kind mentioned in the introductory part is characterized, according to the invention, by an area-elastic pressure means for pressing on the rear face of the electrode element, which rear face is averted from the surface, in such a way that the electrode element can be automatically adapted to irregularities of the surface by local deformation.

The electrode arrangement according to the invention therefore automatically ensures that the electrode element is adapted to irregularities of the surface even when the irregularities have only a small flat extent. Owing to the arrangement according to the invention of an area-elastic pressure means on the rear face of the electrode arrangement, it is ensured that the electrode arrangement continues to exert a uniform contact pressure on the surface to be treated. The "area-elastic" pressure means has the effect that the flat electrode element is pressed uniformly in the direction of the surface which is to be treated, specifically over the entire contact-pressure area with a substantially identical contact-pressure force.

In a preferred embodiment, the contact-pressure force of the area-elastic pressure means can be generated by an elastic material which is fastened in a housing part which serves as a supporting bearing. The housing part can be of rigid design, but also be designed with a certain degree of flexibility, wherein the housing has to be stiffer than the elastic material in order to be able to serve as a supporting bearing. The elastic material, which is preferably a soft-elastic material, can be compressed when the electrode arrangement bears on the surface which is to be treated, with the result that the restoring force of the elastic material creates the surface-active contact-pressure force for the electrode arrangement. If the surface has irregular deformations, the contact-pressure force of the elastic material ensures that the electrode arrangement of flexible configuration can adapt to this formation. It is possible in this way to adapt to irregularities of which the extent in the surface is in the centimeter range down to the range of a few millimeters. The material which creates the contact-pressure force can be normal soft-elastic material in this case, for example formed by an open-cell or closed-cell foamed plastic. The elastic material can also be an elastomeric material. Furthermore, it is possible to design a surface of the material, which surface is perpendicular to the contact-pressure direction, in a profiled manner in order to in this way to control the elastic contact-pressure force depending on the deformation path. Therefore, it is possible, for example, to allow the elastic material on that side which is averted from the electrode arrangement to bear against the housing part by way of conical or rounded projections, so that a progressively increasing restoring force is produced on account of the deformation of the projections.

It is structurally simple to generate the contact-pressure force using a compressible elastic material. However, it is also possible for area-elastic pressure means to be formed from a large number of spring elements which are supported at one end against the housing part, and, with contact surfaces, form a contact-pressure array on the rear face of the electrode device. A pressure device can be formed in the manner of a spring core mattress in this way.

The housing part, which serves as an abutment for the area-elastic pressure means for the contact pressure of the electrode arrangement against the surface, preferably has a flat extent with which it projects beyond the flat extent of the electrode device, preferably on all sides.

The area-elastic pressure means can be formed from a dielectric material which covers the rear face of the electrode arrangement. As a result, it is possible for the electrode to be designed to be thinner and more flexible than the dielectric which covers the surface which is to be treated, because the electrode which carries the high-voltage can be isolated on the rear face at least by the area-elastic pressure means too. Even if the electrode is fully embedded, for example molded, into a dielectric in order to ensure electric shock protection in this way, the pressure means can make a contribution to additional safety.

It is also preferred in the case of the electrode arrangement according to the invention for the effective surface of the dielectric to have a structure which forms intermediate air spaces in which the plasma can be produced when the effective surface bears against the surface which is to be treated. In this case, it is preferred for the structure to have studs, the end faces of said studs being designed to bear against the surface which is to be treated, as is known, in principle, from DE 10 2009 060 627 A1.

BRIEF DESCRIPTION OF THE DRAWING

The invention will be explained in greater detail below with reference to an exemplary embodiment which is illustrated in the drawing.

DETAILED DESCRIPTION

The single drawing FIGURE shows a housing part 1 which is designed in a pot-like manner with a flat bottom wall 2 and a cylindrical circumferential casing wall 3. In this case, the housing part 1 can be designed with a round, rectangular or polygonal cross section. The housing part 1 is designed to be open on that side which is opposite the bottom wall 2 and therefore serves as a receptacle for an area-elastic pressure means 4 in the form of an integrally elastic piece of material, for example composed of a preferably soft-elastic foamed plastic.

The elastic pressure means 4 is provided with a recess of large area on that face which is averted from the bottom wall 2, said recess forming a receiving space 6 which is delimited by a circumferential edge 5. An electrode element 7 which comprises a flat electrode 8 which is surrounded on all sides by a flat and flexible dielectric 9 is inserted in a matching manner into the receiving space 6 which is open on one side. The dielectric 9 projects beyond the edge 5 of the pressure means 4 by way of an effective surface 10. The effective surface 10 is provided with a structure 11 with which it can bear against a surface (not illustrated) which is to be treated. The structure 11 comprises projections 12 between which there are intermediate spaces 13. The intermediate spaces 13 are, for example, filled with air and form the spaces in which the plasma can form when the effective surface 10, by way of the structure 11, bears against the surface which is to be treated.

In the illustrated preferred embodiment, the projections 12 are formed by studs which have planar end faces 14 which are aligned with one another and which, all together, form a contact surface for the surface which is to be treated, for example a skin surface.

The electrode 8 and the dielectric 9 are formed from an easily deformable material and can therefore be adapted to unevennesses of the surface which is to be treated on account of the contact pressure which is generated by the pressure means 4, so that uniform plasma formation in the intermediate spaces 13 is ensured even in the case of surfaces of irregular shape.

A high-voltage connection 15 makes contact with the electrode 8, said high-voltage connection bearing against the electrode by way of a flat end piece 16 which merges integrally into a bolt-like body 17 with which the high-voltage connection 5 is routed through a passage opening 18 in the elastic pressure means 4. Immediate abutment of the bolt-like body 17 against the pressure means 4 is prevented by an insulating sleeve piece 19 which surrounds the bolt-like body 17 within the passage opening 18 of the pressure means 4 and extends as far as the flat end piece 16 of the high-voltage connection 15. An insulating body 20, through which the bolt-like body 17 projects and which extends as far as into an interior space 21 in a metallic high-voltage block 22 which is open at the bottom, is inserted into the housing part 1 in alignment with the bottom wall 2 of the housing part 1. The bolt-like body is supported against an opposite end wall of the interior space 21 by means of a compression spring 23. To this end, the bolt-like body 17 is provided with an end-face termination piece 24, the outside diameter of said termination piece corresponding to the inside diameter of the interior space 21. An electrically conductive, flexible transition piece 25, which bears against the bolt-like body 17 with an inwardly directed prestress and thereby creates an electrical connection between the high-voltage block 22 and the bolt-like body 17 of the high-voltage connection 15, is located between the termination piece 24 and the insulation piece 20. The transition piece 25 can be provided in this case in the manner of a metallic folding bellows or with fins which project inward and are bent radially outward by the bolt-like body 17.

The housing part 1 has, on an angled end piece 26, a recess for a tubular grip part 27. The tubular grip part contains—in a schematically illustrated manner—a high-voltage generator 28 which outputs a high-voltage potential on an output line 29. The output line is connected to the high-voltage block 22 in a conventional manner, with the result that the entire high-voltage block is at the high-voltage potential which is transmitted by means of the transition piece 25 to the high-voltage connection 15, and from there to the electrode 8.

The tubular grip part is terminated at its upper end by a cable bushing 30 for a connection cable 31. The connection cable 31 transports a low voltage of, for example, 6 V which is converted to approximately 400 V in a voltage converter 32 within the grip part 27. This output voltage forms the input voltage for the high-voltage generator 28 which generates a pulsed high voltage by, for example, higher frequency ignition sparks being generated, the current flow of which is transformed up to form high-voltage peaks in a transformer. It goes without saying that all of the other high-voltage generators which are already known can also be used.

The illustrated exemplary embodiment therefore constitutes a handheld device which can be held by way of the—obviously insulating—grip part 27. The power supply to the grip part 27 is a safe low-voltage power line. The high-voltage generation which is required for plasma formation takes place in the grip piece itself. The generated high-voltage reaches the high-voltage block 22 which is securely fastened in the insulating housing part 1 and by means of which the high-voltage potential reaches the high-voltage connection 15 and therefore the electrode 8. The high-voltage generator generates the high-voltage potential, with the result that, for example, for treating a skin surface, said skin surface can act as a counterelectrode for the generated plasma.

The invention claimed is:

1. An electrode arrangement for forming a dielectrical barrier plasma between an effective surface of the electrode arrangement and a surface which acts as a counterelectrode, comprising:
   a flexible, flat electrode connectable to a high-voltage source suitable for forming a plasma;
   a flat, flexible dielectric which forms an effective surface, wherein said dielectric is connected to the flat electrode to form an electrode element and completely covers the electrode with respect to a surface which is to be treated, wherein the electrode element has a rear face; and
   an area-elastic pressure-applying device or material for pressing on the rear face of the electrode element, which rear face is averted from the surface which is to be treated, in such a way that the electrode element is automatically adaptable to irregularities of the surface which is to be treated by local deformation,
   wherein the electrode element is pressed uniformly by the area-elastic pressure-applying device or material in the direction of the surface which is to be treated over an entire contact-pressure area with a substantially identical contact-pressure force,
   wherein the area-elastic pressure-applying device or material is an elastic material which is fastened in a housing part which serves as a supporting bearing.

2. The electrode arrangement as claimed in claim 1, wherein the area-elastic pressure-applying device or material covers the rear face of the electrode element with a dielectric material.

3. An electrode arrangement for forming a dielectrical barrier plasma between an effective surface of the electrode arrangement and a surface which acts as a counterelectrode, comprising:
   a flexible, flat electrode connectable to a high-voltage source suitable for forming a plasma;
   a flat, flexible dielectric which forms an effective surface, wherein said dielectric is connected to the flat electrode to form an electrode element and completely covers the electrode with respect to a surface which is to be treated, wherein the electrode element has a rear face; and
   an area-elastic pressure-applying device or material for pressing on the rear face of the electrode element, which rear face is averted from the surface which is to be treated, in such a way that the electrode element is automatically adaptable to irregularities of the surface which is to be treated by local deformation,
   wherein the electrode element is pressed uniformly by the area-elastic pressure-applying device or material in the direction of the surface which is to be treated over an entire contact-pressure area with a substantially identical contact-pressure force, wherein the area-elastic pressure-applying device or material comprises a plurality of spring elements which are supported at one end against a housing part which serves as a supporting bearing, and, with contact surfaces, form a pressure array on the rear face of the electrode element.

4. The electrode arrangement as claimed in claim 1 wherein the housing part has a flat extent with which it projects beyond a flat extent of the electrode element.

5. The electrode arrangement as claimed in claim 4, wherein the flat extent of the housing part projects beyond the flat extent of the electrode element on all sides.

6. The electrode arrangement as claimed in claim 1 wherein the housing part has an electrical bushing for a high-voltage connection.

7. The electrode arrangement as claimed in claim 1 wherein the effective surface of the dielectric has a structure comprising a plurality of projections which form intermediate spaces therebetween in which the plasma can form when the effective surface bears against the surface which is to be treated by way of the structure.

8. The electrode arrangement as claimed in claim 7, wherein the structure's plurality of projections include studs, the end faces of said studs being configured to bear against the surface which is to be treated.

9. The electrode arrangement of claim 3, wherein the area-elastic pressure-applying device or material covers the rear face of the electrode element with a dielectric material.

10. The electrode arrangement as claimed in claim 3 wherein the housing part has an electrical bushing for a high-voltage connection.

11. The electrode arrangement as claimed in claim 4 wherein the effective surface of the dielectric has a structure comprising a plurality of projections which form intermediate spaces therebetween in which the plasma can form when the effective surface bears against the surface which is to be treated by way of the structure.

12. The electrode arrangement as claimed in claim 11, wherein the structure's plurality of projections include studs, the end faces of said studs being configured to bear against the surface which is to be treated.

* * * * *

UNITED STATES PATENT AND TRADEMARK OFFICE
CERTIFICATE OF CORRECTION

PATENT NO. : 9,345,120 B2  
APPLICATION NO. : 14/419671  
DATED : May 17, 2016  
INVENTOR(S) : Dirk Wandke et al.

Page 1 of 1

It is certified that error appears in the above-identified patent and that said Letters Patent is hereby corrected as shown below:

Please correct the recitation of the Applicant on the title page as follows:

Item 71 Applicant: CINOGY GmbH, Duderstadt (DE)

Signed and Sealed this  
Second Day of August, 2016

Michelle K. Lee  
*Director of the United States Patent and Trademark Office*